United States Patent [19]

Ahrens

[11] Patent Number: 4,935,246

[45] Date of Patent: Jun. 19, 1990

[54] PROCESS FOR THE COATING OF GRANULES

[75] Inventor: Gerhard Ahrens, Kelkheim, Fed. Rep. of Germany

[73] Assignee: Hoechst Aktiengesellschaft, Frankfurt am Main, Fed. Rep. of Germany

[21] Appl. No.: 213,176

[22] Filed: Jun. 29, 1988

[30] Foreign Application Priority Data

Jul. 1, 1987 [DE] Fed. Rep. of Germany ....... 3721721

[51] Int. Cl.$^5$ ............................ A61K 9/16; A61K 9/42
[52] U.S. Cl. ...................................... 424/490; 424/498; 424/502; 427/212; 427/213; 427/240; 428/484
[58] Field of Search ................... 427/213, 212, 240; 424/498, 502; 428/484

[56] References Cited

U.S. PATENT DOCUMENTS

| | | | |
|---|---|---|---|
| 3,009,775 | 11/1961 | Ladenburg | 428/484 |
| 3,119,742 | 1/1964 | Heimlich et al. | 167/82 |
| 4,132,753 | 1/1979 | Blichare et al. | 264/25 |
| 4,533,562 | 8/1985 | Ikegami | 427/212 |

FOREIGN PATENT DOCUMENTS

| | | |
|---|---|---|
| 0168044 | 1/1986 | European Pat. Off. ............ 424/498 |
| 2436052 | 5/1976 | Fed. Rep. of Germany . |
| 2651176 | 3/1977 | Fed. Rep. of Germany . |
| 1077950 | 11/1954 | France . |
| 53-62821 | 6/1978 | Japan . |
| 1044572 | 10/1966 | United Kingdom . |
| 1253067 | 11/1971 | United Kingdom . |
| 1346415 | 2/1974 | United Kingdom . |
| 1560841 | 2/1980 | United Kingdom . |

OTHER PUBLICATIONS

Bauer, Pharm. Ind., vol. 41, No. 10, 1979, pp. 973-976, (English Abstract).

Funakoshi et al., Powder Technology, vol. 27, 1980, pp. 13-21.

Reynolds, Manufacturing Chemist, vol. 41, 1970, pp. 40-43.

*Primary Examiner*—Ellis P. Robinson
*Assistant Examiner*—A. Hulina
*Attorney, Agent, or Firm*—Finnegan, Henderson, Farabow, Garrett, and Dunner

[57] ABSTRACT

A process is described for the coating of granules containing wax-like substances, in an apparatus having a rapidly rotating horizontal disk located in a vertical container, in the presence of one or more wax-like substances or a mixture of one or more was-like substances, wherein the wax-like substances in powder form are scattered onto the granules which have been heated until the wax-like substance has softened.

7 Claims, No Drawings

PROCESS FOR THE COATING OF GRANULES

The invention relates to a process for the coating of granules with substances exclusively in powder form and to the coated granules obtained by this process. The granules are used especially in the pharmaceutical sector.

The coating of spherical granules, undertaken mostly for the purpose of controlling the release of active compounds or masking of an unpleasant taste or imparting resistance to digestive fluids or stabilizing against the effects of environment, is predominantly carried out by pouring on or spraying on of solutions, suspensions or emulsions, or by applying molten coating substances.

In a build-up of granules from an initial particle, which process can likewise be considered as coating of granules, it is true that the addition of the material to be granulated takes place in powder form, but here, too, a liquid medium is indispensable as a binder or binder carrier.

The application of liquid media in the coating of granules takes place by pouring or spraying, preferably, however, by spraying. Spraying requires costly aggregates, at least in the case of molten materials. When solutions, suspensions or emulsions are applied, the liquid auxiliary must again be removed in a time-consuming manner and in many cases, because of environmentally hazardous characteristics of the materials used, it must be disposed of at great expense. Thus, in the case of active compounds which are readily soluble in water, larger amounts of organic solvents are required in particular for applying the final membrane. The application of the coating materials to the granules exclusively in powder form without using liquid auxiliaries which could avoid the above shortcomings, has so far not been described. It is true that electrostatic powder coating has been known for a very long time and is in widespread use, but its conversion into a practical process for the coating of granules is yet to be discovered.

The use of equipment referred to as rotary granulator (K. H. Bauer, Pharm. Ind. 41, 973, (1979)) or centrifugal granulator (Y. Funakoshi, Powder Technol. 27, 13, (1980)) for the coating of granules is well known. The items of equipment mentioned essentially consist of a vertical round container in which there is a horizontal disk, with which the granules rotate while the container is stationary. A stream of air passes through the small slit between the rotating disk and the container wall; the purpose of this air is on the one hand to prevent any material falling through and on the other hand to remove sprayed-on solvent. Spheronizers such as, for example, Marumerizer ® (Reynolds A. D., Manufacturing Chemist. 41, 40, (1970)) from which the rotary granulators have originated, have no facilities for applying or removing greater amounts of drying air. They have been developed for rounding particles of plastic compounds.

The use of wax-like substances for the coating of granules (cf. for example Japanese Patent Application 53-062,821, German Offenlegungsschrift 2,651,176 (=British Patent 1,560,841), U.S. Pat. No. 3,119,742 and British Patent 1,044,572) has also been known for a long time; however, the use of liquid formulations of the coating substances could not be dispensed with.

Surprisingly, it has now been found that it is possible to coat granules by exclusively using substances in powder form.

It is a prerequisite of any application of a substance in powder form to a molding that adequate adhesion to the surface to be coated is provided for. In the build-up of granules, a liquid binder composition is used for this purpose, as already referred to. The problem is solved by the present invention in a most elegant manner by incorporating a wax-like substance into the granules to be coated, and the granules are agitated on the rotating disk with heating. The surface of the granules to be coated becomes tacky due to the softening of the wax-like auxiliary and is ready to accept coating substances in powder form without addition of liquid and without the particles adhering to one another.

Accordingly, the invention relates to a process for the coating of rounded or non-rounded granules, prepared in the conventional manner and containing wax-like substances, in an apparatus having a rapidly rotating horizontal disk located in a vertical container, in the presence of one or more wax-like substances or a mixture of one or more wax-like substances, which process comprises scattering the wax-like substances in powder form onto the granules which have been heated until the wax-like substance has softened. If desired, the wax-like substances in admixture with one or more active compounds and, if desired, one or more nonwax-like auxiliaries may be scattered by rotating the disk.

The process is preferably carried out in a spheronizer (e.g. Marumerizer), a rotary or centrifugal granulator. Heating is achieved, for example, by means of a stream of hot air or an infra-red lamp.

Wax-like substances are understood in the foregoing and subsequent statements to be natural, semi-synthetic and synthetic waxes. They have hydrophobic or hydrophilic characteristics. The release of active compounds is influenced by the content of wax-like substance or a mixture of wax-like substances present in the granules or in the coating; it can be retarded by suitable substances. Suitable wax-like coating substances are especially fatty alcohols and their derivatives, fatty acids and their derivatives, hydrocarbons, waxes and polyethylene glycols and their derivatives having a melting point in excess of 20° C.

Granules produced in the conventional manner are, for example, melt granules, granules produced in the dry or in the moist, or small extrudates.

The granules to be coated also contain, in addition to the wax-like auxiliary, the active compound or compounds. The wax-like coating material in powder form may also contain one or more active compounds. The coating and the granules may contain the same or different active compounds. The process according to the invention is especially suitable for the coating of granules of active compounds which are freely soluble in water.

The granules as well as the coating material may contain further generally customary non-wax-like auxiliaries which are water-soluble or water-insoluble. They may also be compounds which swell in water.

When carrying out the process, it is expedient to give the particles of the granules to be coated a spherical shape prior to the coating step by prolonged rotation and heating with plastic deformation. This is particularly expedient when a uniform coating thickness is to be produced.

A further prerequisite for the success of applying materials in powder form is rapid distribution of the coating substances over the whole surface to be coated which in the present process is achieved by using the rotating disk. Any self-agglomeration of the added powder therefore cannot occur, as would be the case with a slowly rotating barrel.

The layer of powder loosely applied to the granules must be converted to a dense, continuous coat, especially when it has to function as the membrane. Furthermore, the subsequent powder coat must adhere.

Both problems are solved by incorporating a wax-like substance into the mixture of the coating substances.

Heating leads to softening of the wax portion which coalesces by the rotary motion to a dense coating and provides adhesion for the subsequent layer.

If the coating to be applied by the process according to the invention is intended to control the release of active compounds from the granules or to mask an unpleasant taste or to impart resistance to digestive fluids or to stabilize against the effects of the environment, it is often desirable that the uncoated granule particle allows undelayed active compound release. The wax-like substance required for carrying out the process within the granule particle must in such cases therefore not retard release. Polyethylene glycols which come into consideration for this purpose, are by themselves unsuitable, since granules produced with them cannot be made spherical on the rotating disk by the effect of heat without the particles adhering to one another by plastic deformation. Furthermore, the mixture of the coating substances containing hydrophobic wax-like substances for attaining the above aims, does not adhere to the surface of such granules. It has now been found that granules which are on the one hand highly suitable for the process but on the other hand do not retard the release of active compounds, are obtained when polyethylene glycols as hydrophilic wax-like substances as well as hydrophobic wax-like substances, as contained in the mixture of coating substances, are incorporated into the granules.

In detail, the process is performed in such a way that, for example, the granules to be coated, prepared in conventional manner, are rotated in equipment of the spheronizer type and at the same time heated by a stream of hot air or by infra-red lamp irradiation until softening sets in. This point in time can in general be identified by a change in shape of the rotating material which takes on a tubular shape. Further heating is carried out very carefully to prevent the particles adhering to one another. If required, the rotary motion is continued under controlled heating conditions until the desired degree of roundness is achieved.

A powder composed of a pure wax-like substance or of pure wax-like substances, or a powder mixture composed of active compounds and a wax-like substance, or a powder mixture composed of a wax-like substance and non-wax-like auxiliaries and, if desired, of active compounds, is applied to the non-rounded granules or to granules rounded as above which have been heated until softening sets in. By alternating addition of powder and heating or by simultaneous addition of powder and heating, with the heat inlet and powder inlet positions being separate, the respective layers can be built up to the desired thickness.

EXAMPLE 1

Melt granules (fraction 0.75–1.25 mm) composed of
100 g of furosemide
100 g of paraffin wax (Special Wax 4900) and
100 g of sodium carboxymethyl cellulose (Methocel K15M)
were rotated in a spheronizer with a disk of about 22 cm in diameter at about 250 rpm and were heated using a commercially available hot-air gun until softening of the material had set in, this being recognisable by the different running characteristics of the material. Subsequently the rate of revolution was increased to about 800 rpm and a part quantity of a powder mixture composed of
200 g of furosemide
200 g of paraffin wax (Special Wax 4900)
200 g of sodium carboxymethylcellulose (Methocel K15M) and
30 g of sodium dihydrogen phosphate
was scattered on until the slight tackiness of the granule particles, recognisable by special running characteristics of the material, had ceased. Subsequently heating was resumed until the particles commenced to be tacky and more of the powder mixture was added. The process was continued until the whole of the powder was applied.

The sieve fraction of 1.0–1.25 mm was tested for active compound release in a paddle apparatus in accordance with USP XXI:
Amount weighed: 184.5 mg of spherical granules
Rate of rotation: 50 rpm
Dissolution medium: phosphate buffer ph 5.8.
The following amounts of furosemide were cumulatively released:
1st hour 7.0%
2nd hour 20.9%
3rd hour 36.0%
4th hour 48.6%
5th hour 61.6%
6th hour 71.9%.

EXAMPLE 2

Melt granules (fraction 0.75–1.25 mm) composed of
225 g of Metamizol
39.6 g of paraffin wax (Special Wax 4900) and
35.4 g of polyethylene glycol 6000
were heated under the same conditions as in Example 1 with rotation, and a first powder mixture composed of
45 g of Metamizol
7.05 g of paraffin wax (Special Wax 4900) and
7.95 g of polyethylene glycol 6000 was applied.
Subsequently, again under the same conditions, a second powder mixture, composed of
75 g of paraffin wax (Special Wax 4900)
24 g of micronized lactose and
1 g of red iron oxide
was applied.

The sieve fraction 1.0–1.25 mm was tested for active compound release in a basket apparatus in accordance with USP XXI:
Amount weighed: 127.77 mg of spherical granules
Rate of rotation: 100 rpm Dissolution medium: simulated gastric fluid pH 1.2.
The following amounts of Metamizol were cumulatively released:
1st hour 8.0%
2nd hour 17.2%
3rd hour 28.8%
4th hour 40.9%
5th hour 52.1%

6th hour 61.3%.

EXAMPLE 3

The process was carried out as described in Example 2 including the application of the first powder mixture and then, under the same conditions as in Example 2, a second powder mixture consisting of
50 g of paraffin wax (Special Wax 4900)
16 g of micronized lactose and
0.66 g of red iron oxide was applied.

Active compound release was determined under the same conditions as in Example 2:
Amount weighed: 118.52 g of spherical granules
1st hour 17.7%
2nd hour 34.6%
3rd hour 49.3%
4th hour 64.0%
5th hour 74.1%
6th hour 79.0%.

I claim:

1. A process for coating a rounded or non-rounded granule in an apparatus having a rapidly rotating horizontal disk located in a vertical container, which comprises scattering a wax-like substance or a mixture of wax-like substances in powder form and in the absence of liquid onto the granule, said granule containing a wax-like substance and being heated until the wax-like substance contained therein has softened.

2. The process as claimed in claim 1, wherein the wax-like substance or mixture of wax-like substances is scattered in admixture with one or more active compounds.

3. The process as claimed in claim 1, wherein the granule is given a spherical shape, prior to the coating, by prolonged rotation and heating with plastic deformation.

4. The process as claimed in claim 1, wherein the granule to be coated contains a hydrophobic wax-like substance or a mixture of hydrophilic and hydrophobic wax-like substances.

5. The process as claimed in claim 1, wherein fatty alcohols or their derivatives, fatty acids and their derivatives, hydrocarbons, waxes or polyethylene glycols and their derivatives having a melting point in excess of 20° C. are used as the wax-like substance.

6. A granule having a wax-like coating, obtainable by the process according to claim 1.

7. The process of claim 2, wherein the substance further contains a non-wax-like auxiliary.

* * * * *